US 6,648,887 B2

(12) United States Patent
Ashman

(10) Patent No.: US 6,648,887 B2
(45) Date of Patent: Nov. 18, 2003

(54) VARIABLE ANGLE SPINAL IMPLANT CONNECTION ASSEMBLY

(76) Inventor: Richard B. Ashman, 1407 First St., New Orleans, LA (US) 70130

( * ) Notice: Subject to any disclaimer, the term of this patent is extended or adjusted under 35 U.S.C. 154(b) by 10 days.

(21) Appl. No.: 10/055,050

(22) Filed: Jan. 23, 2002

(65) Prior Publication Data

US 2003/0139745 A1 Jul. 24, 2003

(51) Int. Cl.[7] .............................................. A61B 17/70
(52) U.S. Cl. ......................................... 606/61; 606/72
(58) Field of Search ............................. 606/60, 61, 72, 606/73; 623/17.11

(56) References Cited

U.S. PATENT DOCUMENTS

| | | | |
|---|---|---|---|
| 5,002,542 A | * 3/1991 | Frigg | 606/61 |
| 5,047,029 A | 9/1991 | Aebi et al. | |
| 5,242,445 A | 9/1993 | Ashman | |
| 5,261,909 A | 11/1993 | Sutterlin et al. | |
| 5,282,801 A | 2/1994 | Sherman | |
| 5,380,323 A | 1/1995 | Howland | |
| 5,487,742 A | 1/1996 | Cotrel | |
| 5,643,263 A | 7/1997 | Simonson | |
| 5,885,285 A | * 3/1999 | Simonson | 606/61 |
| 6,132,430 A | * 10/2000 | Wagner | 606/61 |
| 6,183,473 B1 | * 2/2001 | Ashman | 606/61 |
| 6,210,413 B1 | * 4/2001 | Justis et al. | 606/61 |

FOREIGN PATENT DOCUMENTS

| | | | | |
|---|---|---|---|---|
| WO | WO 01/67972 | * 9/2001 | | A61B/17/70 |

* cited by examiner

Primary Examiner—Pedro Philogene
Assistant Examiner—Michael B. Priddy
(74) Attorney, Agent, or Firm—Maginot, Moore & Bowman, LLP

(57) ABSTRACT

A variable angle clamp is provided for use with a spinal implant assembly having a spinal rod, a Schantz screw having an elongated shank, and a variable angle connector receiving the spinal rod and having a washer mounted on the body with a first surface defining a variable angle feature, and a stem projecting from the body, the stem terminating in a T-bar having a second surface facing the first surface. The variable angle clamp includes a clamping portion defining a bore configured to receive the shank Schantz screw therein. The clamp further includes a pair of clamp halves forming a slot therebetween that intersects the bore in the form of a split clamp. An outer surface of one of the clamp halves defines a variable angle feature for interengagement with the first surface of the washer. The outer surface of the other of clamp half is configured for pressure contact with the second surface of the T-bar. The clamp halves define an open channel configured to receive the stem of the variable angle connector therein when the shank of the bone-engaging fastener extends through the clamping bore.

20 Claims, 3 Drawing Sheets

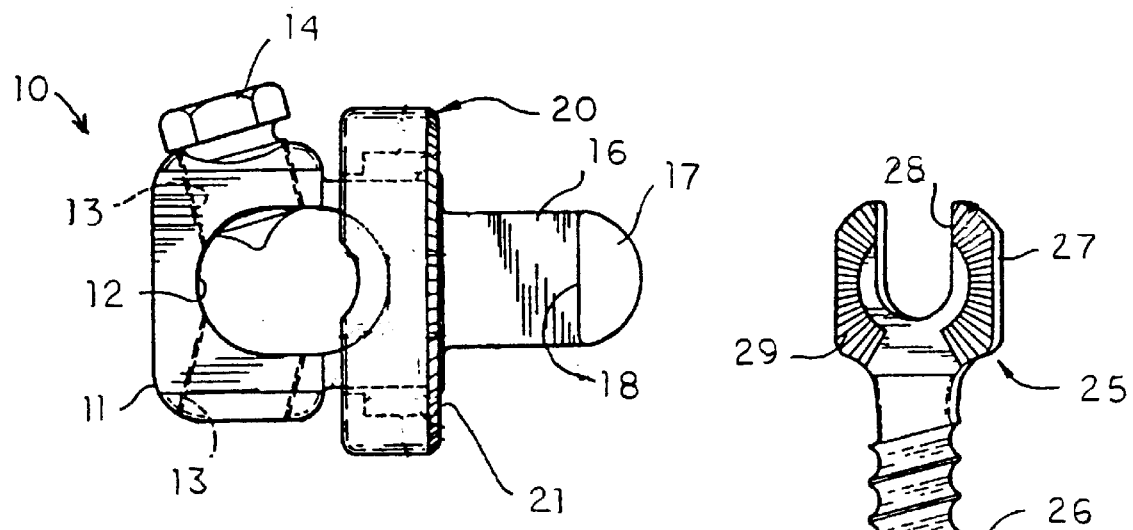
FIG. 1
(PRIOR ART)
FIG. 2
(PRIOR ART)
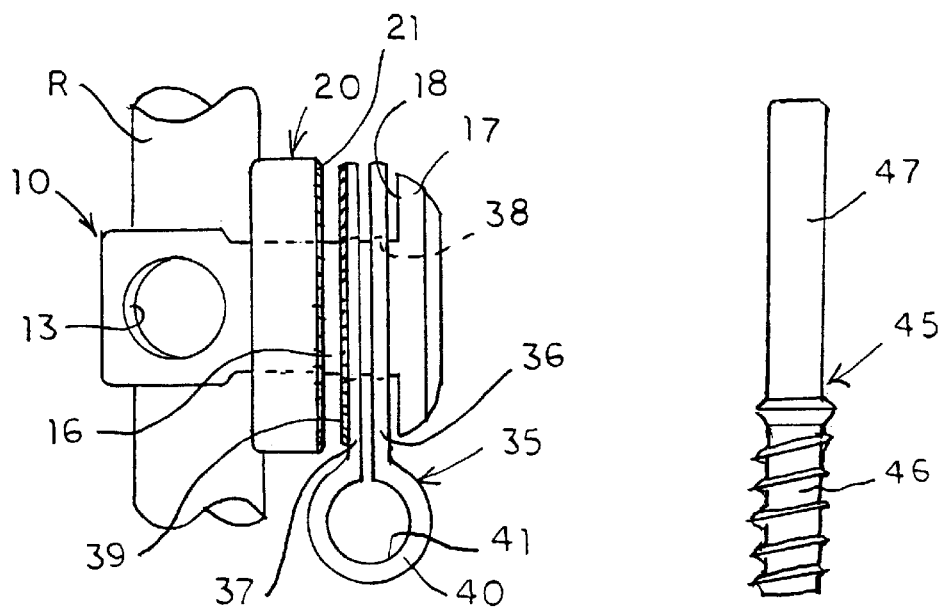
FIG. 3
(PRIOR ART)
FIG. 4
(PRIOR ART)

VARIABLE ANGLE SPINAL IMPLANT CONNECTION ASSEMBLY

BACKGROUND OF THE INVENTION

The present invention relates generally to the field of spinal implant systems, and particularly to systems that employ elongated spinal implants, such as rod and plates, connected at various locations along the spinal column. More particularly, the invention concerns a connection assembly that provides variable angle adjustability to the elongated spinal implant relative to a bone fastener engaged to the spine.

Several spinal fixation systems have been developed for use in correcting and stabilizing sections of the spinal column and facilitating spinal fusion. In one such system, a bendable elongated spinal implant, such as a rod, is longitudinally disposed adjacent the vertebral column and then secured to various vertebrae along the length of the column by way of a number of bone fasteners of fixation elements. A variety of bone fasteners can be utilized, such as hooks or bone screws, which are configured to engage specific portions of a vertebra.

An example of one such system is the TSRH® Spinal System of Sofamor Danek Group, Inc. In this system, various hooks and bone screws are engaged to a spinal rod by way of eyebolts. In early versions of the TSRH® Spinal System, the vertebral hooks and bone screws were attached to the spinal rod at a fixed orientation, usually projecting perpendicularly below the rod. At the time, the TSRH® Spinal System presented a significant advance over prior systems in its VERSATILITY, strength of fixation, and ease of implantation.

However, one drawback faced by the original TSRH® Spinal System, as well as the other prevalent fixation systems, was that the surgeon was required to make significant adjustments to the contour of the bendable rod so that the bone fasteners could solidly engage the vertebra bodies. What was needed, then, was a bone fastener that could be connected to the spinal cord a variable angle. In order to address this need, the TSRH® Variable Angle Screw was developed, as described in U.S. Pat. No. 5,261,909. This Variable Angle Screw utilized the same TSRH® eyebolt to achieve a connection to a spinal rod. In addition, the Variable Angle System incorporated a washer that fit over the eyebolt, engaged the spinal rod within a groove in one surface of the washer, and provided a radially splined surface facing the bone fastener. The bone fastener had a complementary splined surface so that the fastener could be situated at variable angular orientations relative to the spinal rod. A nut threaded onto the post of the eyebolt clamped all the components together to complete the assembly.

The Variable Angle Screw system of the '909 Patent presented a significant advance over prior rod-based implant systems. The system of the '909 Patent was relatively compact and required a minimal number of parts, yet was able to accomplish a solid fixation of the bone fasteners to the rod at a wide range of angular orientations. One drawback of the system was that the eyebolt-nut combination required side tightening of the nut to clamp the system together. This side-tightening aspect required a larger surgical site about the spine so that a wrench could be manipulated. To address this difficulty, a top-tightening assembly was developed as disclosed in U.S. Pat. No. 5,282,801. The clamp assembly depicted in the '801 Patent replaced the eyebolt and nut with a clamp body having a T-bar against which the head of the variable angle bone fastener was clamped. In addition, while the original TSRH® System relied upon tightening a nut against the variable angle bone screw, the top-tightening approach of the '801 Patent utilized a set screw that acted against the spinal rod to push the spinal rod into the interlocking washer, and ultimately against a complementary spline face of the variable angle screw. With this system, the variable angle capability was retained, while a top-tightening feature was added.

With the addition of the top-tightening capability, the more recent TSRH® Spinal System has provided surgeons with a great deal of flexibility in the placement and orientation of bone fasteners, such as hooks and screws, relative to a spinal rod. The variable angle components greatly reduce the need to manipulate and bend the spinal rod to conform to the patient's anatomy. Even with the great improvements presented by the TSRH® Spinal System, a certain amount of shaping or contouring of the spinal rod has still been required. Specifically, the rod must be shaped so that the point of attachment of the bone fastener to the rod is the same distance from the vertebral body as the splined or interdigitating portion of the bone fastener. This vertical or height adjustment is necessary so that the variable angle components are properly aligned for accurate connection when the assembly is clamped to together.

In order to address this difficulty, later systems were developed that provided for a certain degree of vertical adjustability. By vertical or height adjustability, it is meant adjustment along the length of the bone fastener. Adjustment in this dimension allows the rod to be situated at varying distances from the spine, or oriented with a pre-set contour regardless of the location of the fastener.

One approach to achieving vertical adjustability has been to adapt a Schantz-type bone fastener to the variable angle and top-tightening TSRH® System, such as described in the above-mentioned '801 Patent. A Schantz-type fastener includes an elongated smooth shank portion. Adapting this type of fastener to the TSRH® System required the addition of a split clamp that fit over the T-bar of the connector. The split clamp defined a bore to receive the shank of the Schantz-type fastener, in which the bore diameter is effectively reduced around the shank as the split clamp halves are pressed together. One of the clamp halves included an interdigitating feature to engage the variable angle washer. As with the system described in the '801, the top-tightening setscrew is tightened against the rod, which pushes the washer against the split clamp to compress the clamp halves between the washer and the T-bar.

This split clamp has allowed use of a Schantz-type bone fastener, such as a bone screw, to introduce vertical adjustability to the angular adjustability present in the TSRH® System. In addition, the split clamp can be adapted to the top-tightening aspect of the TSRH® System as reflected in the '801 Patent. One difficulty that remains is that the overall construct still embodies a certain amount of "fiddle factor"to implant and connect together. In addition, the addition of the split clamp does not reduce the overall prominence of the construct. There remains a need for a connector assembly that can accommodate a Schantz-type bone fastener while addressing the drawbacks of these prior systems.

SUMMARY OF THE INVENTION

To address this need, the present invention contemplates a connector assembly that includes a variable angle clamp configured to engage the shank of a Schantz-type bone fastener. The clamp includes a pair of clamp halves forming a slot therebetween that intersects a clamping bore configured to receive the bone fastener. Thus, the clamp can be in the form of a split clamp in which the clamp halves are compressed together to reduce the bore and provide a clamping force on the shank of the bone fastener within the bore.

In one important feature of the invention, the clamp halves define an open channel that is configured to receive the stem portion of a connector that provides a link to an elongated spinal implant, such as a spinal rod. In certain preferred embodiments, the clamp and open channel can be configured to be mounted on a variable angle top-tightening connector of the type described in U.S. Pat. No. 5,282,901. However, the clamp halves and open channel can alternatively be configured to mate with other connectors that provide a means to connect the clamp, and ultimately the bone fastener, to an elongated implant.

Each of the clamp halves includes an outer surface against which a clamping force is applied to compress the split clamp against the bone-engaging fastener. The outer surface of one or both of the clamp halves is provided with a variable angle feature. In a preferred embodiment, this feature can include radiating splines that are configured to interdigitate with similar radiating splines on a component of the variable angle connector. The outer surface of the other clamp half can provide a pressure surface and need not, but may, include similar variable angle features.

In accordance with certain features of the invention, the variable angle clamp can be mounted on the shank of a bone-engaging fastener with the open channel exposed. A connector mounted on an elongated implant, such as a spinal rod, can be manipulated to engage the channel of the clamp. The clamp is juxtaposed with the connector at whatever orientation is assumed by the bone-engaging fastener. The entire assembly is tightened so that the clamp halves are compressed to lock the clamp about the fastener.

One object of the invention is to provide a variable angle clamp for use with a bone-engaging fastener having a shank, such as a Schantz-type fastener. Another object is achieved by features that reduce the "fiddle factor" associated with completing a spinal fixation construct.

One benefit of the present invention is that it can be readily used to engage a bone fastener to a spinal rod, for instance. A further benefit is that the inventive variable angle clamp can assume various orientations to facilitate overall assembly of the clamp, connector, spinal rod and bone-engaging fastener.

Other objects and benefits of the invention will become apparent from the following written description taken together with the accompanying figures.

DESCRIPTION OF THE FIGURES

FIG. 1 is a side elevational view of a top-tightening variable angle connector assembly according to a prior system disclosed in U.S. Pat. No. 5,282,801.

FIG. 2 is a side perspective view of a known variable angle bone screw for use with the connector assembly shown in FIG. 1.

FIG. 3 is a variable angle connector assembly modified from the assembly shown in FIG. 1 to accommodate a Schantz screw.

FIG. 4 side elevational view of a portion of a Schantz screw for use with the connector assembly shown in FIG. 3.

DESCRIPTION OF THE PREFERRED EMBODIMENTS

Figure 5:
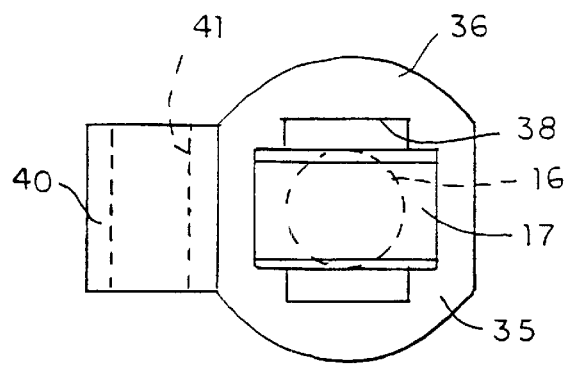
FIG. 5 is a transverse elevational view of the clamp assembly shown in FIG. 3.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Although the present invention has broad applicability, it may be best understood with reference to prior spinal implant connection assemblies, and particularly variable angle connection assemblies. For instance, a representative top-tightening variable angle clamp assembly is depicted in FIG. 1. The connector assembly 10 can be constructed as described in U.S. Pat. No. 5,282,801, the disclosure of which is incorporated herein by reference. In particular, the connector assembly includes a connector body 11 that defines an elongated channel 12 for receiving a spinal rod therethrough. A pair of fixation screw bores 13 are defined in opposite top and bottom surfaces of the body and intersect the elongated channel rod 12. A setscrew 14 can be threaded into one of the screw bores 13 to bear against a rod disposed within the channel.

The top-tightening connector 10 also includes a stem 16 that projects from the body 11. The stem terminates in a T-bar 17 which forms a clamping surface 18.

The variable angle capability of the connector assembly 10 is accomplished by a variable angle washer 20. The washer 20 fits over a portion of the body 11 and can be slid over the T-bar 17 and stem 16 to its operative position. The washer 20 defines a splined surface 21 that can mate with a corresponding splined surface on a spinal fixation element. One such element is depicted in FIG. 2. Specifically, a variable angle screw 25 includes a threaded shank 26 adapted for engagement into a vertebra. The head 27 of the screw 25 defines a yoke opening 28 that is configured to receive the stem 16 of the top-tightening connector of body 11. The head 27 also defines the splined surface 29 that is arranged for mating engagement or interdigitation with the splined surface 21 of the variable angle washer.

The use and application of the top-tightening connector 10 and the variable angle screw 25 is described in more detail in U.S. Pat. No. 5,282,801, the description of which is incorporated here in by reference. Briefly, the variable angle screw 25 can be engaged in a spinal element, such as a vertebra, with the head 27 projecting therefrom. A top-tightening connector 20 can be threaded onto the spinal rod prior to implantation. The connector 10 can be oriented on the rod immediately adjacent the variable angle screw 25, and more particularly with the stem 16 extending through the yoke opening 28 of the screw. The variable angle washer 20 can contact the splined surface 29 of the screw at whatever angular orientation exists between the connector 10 and screw 25. When the setscrew 14 is tightened, it pushes the spinal rod against one side of the washer, which causes the splined surface to press against the variable angle screw. The screw is then trapped between the splined surface 21 of the washer 20 and the clamping surface 18 of the T-bar 17. With this approach, the variable angle screw is solidly affixed to the spinal rod at whatever angular orientation exists between the two components.

While the top-tightening variable angle aspect of the system described in the '801 patent was an important advancement, it was generally limited to bone fixation elements, such as the screw 25, having a head such as the head 27 configured as shown in FIG. 2. In certain applications, a Schantz-type screw may be preferable. In order to address this type of fixation element, an alternative connector or clamp assembly was developed as shown in FIG. 3. In particular, the same top-tightening connector 10 can be mounted on a spinal rod R. In addition, the same variable angle washer 20 can be mounted on the connector body. However, instead of mating directly with the head of a variable angle screw, this prior art system utilized a clamp 35 configured to be mounted over stem 16 of the connector 10. In particular, the clamp included opposite clamp halves 36 and 37. A stem bore 38 is formed through each of the clamp halves 36 and 37 to allow the clamp 35 to be mounted onto the stem 16 of the connector 10.

The clamp 35 further includes a clamping portion 40 that is configured to receive and engage the shank of a Schantz screw, such as a screw 45 shown in FIG. 4. The Schantz screw 45 includes bone engaging thread 46 and a clamping shank 47. The clamping portion 40 of the clamp 35 defines a bore 41 therethrough adapted to receive the clamping shank 47 of the screw 45.

The clamp 35 does not alter the operation of the top-tightening connector 10 from what was described previously. However, as the setscrew is tightened to push the rod R against the washer 20, the washer compresses the two clamp heads 36 and 37 toward each other. When the halves are pushed together, they tend to reduce the diameter of the screw bore 41, which creates an engagement or fixation force against the clamping shank 47 of the Schantz screw 45. Thus, the same top-tightening feature, along with the variable angle engagement feature, can be utilized to engage a Schantz screw clamp, such as clamp 35.

One problem with the Schantz screw clamp 35 may be best understood with reference to FIG. 5. In particular, in order to be mounted over the T-bar 17, the clamp 35, and more particularly each of the clamp halves 36 and 37, must include a stem bore 38 that is sized to fit over the T-bar 17. Thus, in the illustrated assembly the T-bar 17 has a generally rectangular configuration, so the stem bore 38 has a commensurate rectangular configuration. The clamp 35, just as with the variable angle washer 20, is first mounted over the T-bar 17 with the stem bore 38 oriented parallel to the long axis of the T-bar. Then, when in use the clamp 35 is rotated 90° so that the clamp 35 is trapped against the T-bar and engaged over the stem 16.

As can be appreciated, this configuration of the clamp 35 increases the profile or prominence of the clamp because a sufficient material must surround the stem bore 38 to ensure the strength of the clamp. In addition, the bore 38 may require significant manipulation of the clamp 35 to engage the clamp on the T-bar. As discussed in more detail in the '801 patent, the variable angle washer 20 can be preassembled and staked onto the top-tightening connector body 11. Thus, the connector and washer are provided as a single piece during the implantation surgery. The clamp 35 is preferably provided as a separate piece and then engaged onto both the Schantz screw 45 and the stem 16 of the top-tightening connector 10 in situ. The closed opening of the stem bore 38 provides a great deal of the security of the fixation, but also increases the "fiddle factor" associated with completing the variable angle assembly.

Figure 6:
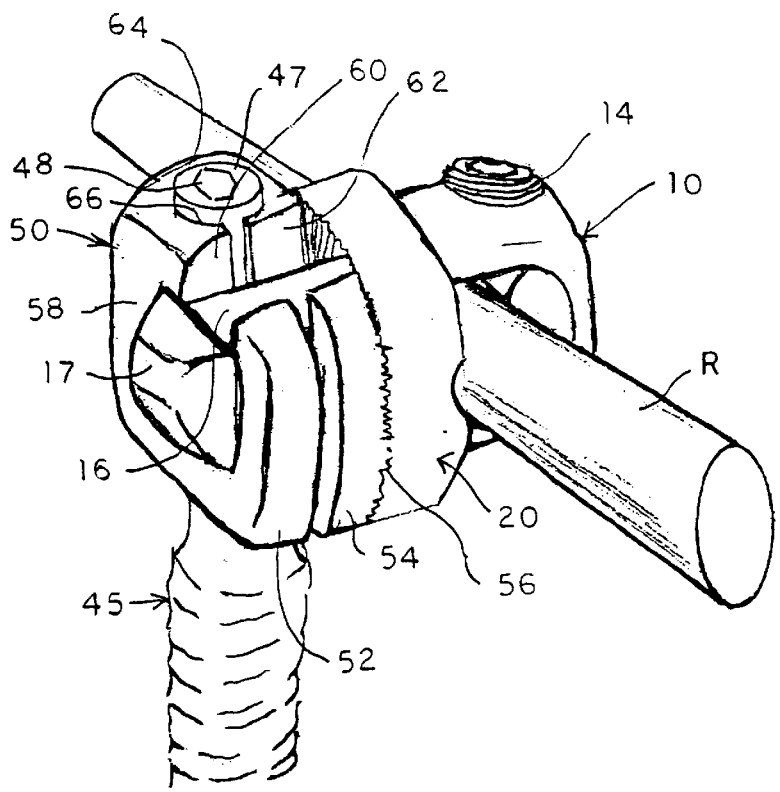
FIG. 6 is a top perspective view of a variable angle connector assembly according to one embodiment of the present invention.

In order to address this problem, the present invention contemplates a variable angle clamp 50, such as the clamp depicted in FIG. 6. Again, the clamp 50 is preferably configured to work with both the top-tightening connector 10 and the variable angle washer 20. As shown in FIG. 6, the variable angle clamp 50 includes opposing clamp halves 52 and 54 that form a slot 55 therebetween so that the clamp can be in the form of a split clamp. The clamp half 54 defines a splined surface 56 configured for engagement or interdigitation with the splined surface of the variable angle washer 20. The opposite clamp half 52 defines an outer clamping surface 58 that is configured for engagement with the clamping surface 18 of the T-bar 17. In the illustrated embodiment, the surface 58 is generally smooth; however, the surface can be configured to enhance engagement with the clamping surface 18. Moreover, a variable angle feature can be incorporated between the surfaces 18 and 58. Alternatively, the variable angle feature can be incorporated into the surfaces 56 and 58 to allow assembly of the clamp in opposite directions—i.e., with the bone screw above or below the T-bar.

In contrast to the clamp 35 depicted in FIGS. 3 and 5, the variable angle clamp 50 according to the preferred embodiment of the present invention defines a yoke channel 60 and 62 through each corresponding clamp half 52, 54. Thus, as shown in FIG. 6, each yoke channels 60, 62 is open so that the stem 16 of the top-tightening connector 10 can readily slide into the channel.

The variable angle clamp 50 further includes a clamping portion 64. The clamping portion defines a screw bore 66 that is sized to receive the shank of a Schantz screw, such as the screw 45 depicted in FIG. 4. As with the clamp 35, the screw bore 66 initially has a diameter that is slightly larger than the diameter of the clamping shank 47 of the screw 45. However, when the variable angle clamp 50 is engaged within the top-tightening connector, and more particularly between the T-bar 17 and the variable angle washer 20, the two clamp halves 52, 54 are driven together, reducing the slot 55 and the diameter of the screw bore 66 to compress or clamp against the shank 47.

Figure 8:
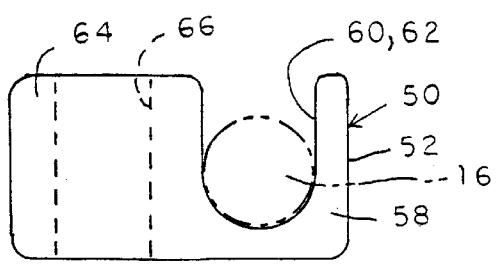
FIG. 8 is a transverse elevational view of the clamp shown in FIG. 7, with the stem of a connector depicted in phantom lines.
Figure 9:
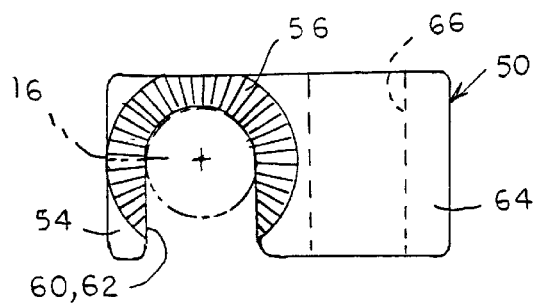
FIG. 9 is a transverse elevational view of the opposite side of the clamp shown in FIGS. 7 and 8, with the clamp in a different orientation.

Certain benefits of the variable angle clamp 50 can be appreciated upon consideration of the opposite side views of FIGS. 8 and 9. As shown in FIG. 8, the stem 16 of the top-tightening connector can be readily and easily slid into the yoke channels 60, 62. With this approach, the clamp 50 need not be preloaded onto the T-bar, but instead can be mounted first onto the screw 45, with the shank 47 extending through the screw bore 66. With the variable angle clamp 50 arranged as shown in FIGS. 6 and 8, that is with the yoke channels 60, 62 facing upward, a top-tightening connector can be slid along the spinal rod R immediately adjacent the clamp 50. The connector can then be rotated about the rod R so that the stem 16 rotates and slides into the yoke channels 60, 62, until the stem is situated at the base of the channel as depicted in phantom lines in FIG. 8. With this feature—i.e., the open yoke channel—the T-bar 17 of the top-tightening connector 10 does not interfere with or complicate the engagement of the variable angle clamp 50 to the connector.

Moreover, as illustrated in FIG. 9 the variable angle clamp 50 can be situated essentially upside down. In other words, the clamp can be mounted on the stem 16 from above so that the openings of the yoke channels 60, 62 face downward. With this approach, a variable angle clamp 50 can be mounted essentially simultaneously over both the clamping shank 47 of the screw 45 and the stem 16 of the top-tightening connector 10. Thus, it can be appreciated that the variable angle clamp 50 provides a greater degree of flexibility in creating a support scaffold for the spine using a spinal rod construct.

It can also be appreciated that the variable angle clamp 50 of the present invention allows flexibility in the placement of the bone fastener, such as the screw 45. For instance, the screw 45 can be threaded into a spinal element, such as a vertebra, while the clamping shank 47 extends through the screw bore 66 of the clamp 50. The screw 46 can be provided with a driving feature 48 in the clamping shank 47 to allow rotation of the screw. This driving feature 48 can be an internal feature for engagement by a driving bit such as a hex tool, or can be an external feature, such as an external hex configuration, for engagement by a wrench. In addition, the driving feature 48 can include a torque-limiting aspect in which the upper portion of the shank 47 is severed from the remainder of the shank at a pre-determined torque. Preferably, the shank of the screw 45 extends only a minimal amount beyond the variable angle clamp 50, thereby reducing the overall profile of the construct.

Figure 10:
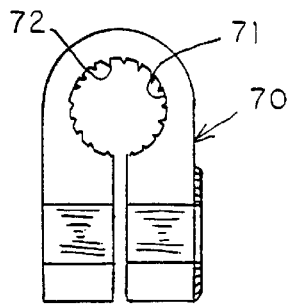
FIG. 10 is a top elevational view of a modified clamp according to a further embodiment of the invention that can be used with the connector assembly shown in FIG. 6.
Figure 11:
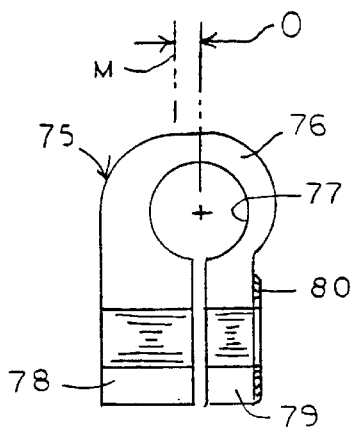
FIG. 11 is a top elevational view of a modified clamp according to another embodiment of the invention that can be used with the connector assembly shown in FIG. 6.
Figure 12:
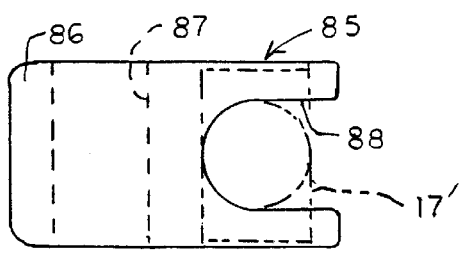
FIG. 12 is a transverse elevational view of a modified clamp in accordance with yet another embodiment of the invention that can be used with the connector assembly shown in FIG. 6.

Additional embodiments of the variable angle clamp of the present invention are shown in FIGS. 10–12. In one alternative embodiment, a clamp 70 can be provided in which the screw bore 71 includes a fixation feature 72. For instance, the fixation feature can be knurling or splines arranged to provide a solid engagement with the clamping shank 47.

Figure 7:
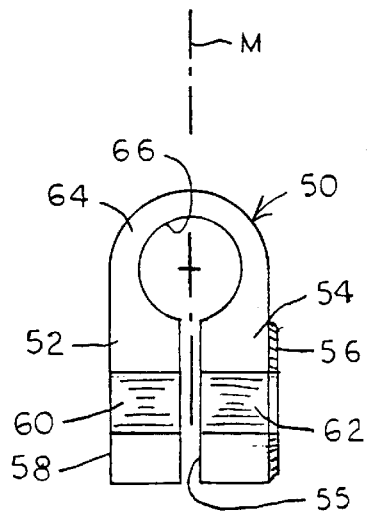
FIG. 7 is a top elevational view of a clamp of the connector assembly shown in FIG. 6.

In the initial embodiment depicted in FIG. 7, the two clamp halves 52 and 54 form a slot 55. This slot 55 intersects the clamping bore 66 to form the split clamp feature. Most preferably, the bore 66 is symmetric about the slot 55 so that an even clamping force is exerted on the shank 47 extending through the bore when the clamp halves are compressed together. In this preferred embodiment, the center of the bore 66 is oriented along the midline M of the clamp 50. In addition, in this preferred embodiment, the clamp halves 52, 54 are generally symmetric. With symmetric clamp halves, the bore in this preferred embodiment is substantially symmetrically disposed between the outer engagement surfaces of the clamp halves.

In an alternative embodiment shown in FIG. 11, a variable angle clamp 75 can include an offset clamping portion 76. More particularly, the portion can be offset so that the screw bore 77 is offset by a dimension O from the midline M of the clamp. With this configuration, the clamp halves 78 and 79 are preferably non-symmetric. Specifically, one clamp half 78 is thicker than the opposite clamp half 79. However, both clamp halves 78 and 79 operate in the same way to perform the clamping function. Of course, it is understood that the offset clamping portion 76 can be configured so that the bore 77 is offset toward the clamp half 78 and away from the variable angle surface 80. With this embodiment, then, the clamping bore is asymmetrically disposed between the outer engagement surfaces of the clamp halves.

As a further alternative, a variable angle clamp 85 can be provided in which the yoke channel opens in a different orientation from the clamp 50. The clamp 85 as illustrated in FIG. 12 includes a clamping portion 86 that defines a clamping bore 87 therethrough. The clamp also includes a yoke channel 88 that is oriented at a generally perpendicular angle to the clamping bore 87. This orientation is in contrast to the substantially parallel arrangement of the yoke channels 60, 62 relative to the clamping bore 66 of the clamp 50 shown in FIGS. 6–9. Again, the yoke channel 88 is configured to receive the stem of a connector, such as connector 10; however, the T-bar of the connector should be rotated, such as the T-bar 17' shown in FIG. 12 to provide solid engagement with the clamp 85.

The variable angle clamp 85 of the embodiment in FIG. 12 can include features similar to those described above, the only difference since the clamp is essentially side-loaded onto the stem of the connector. This side loading capability is made possible by the open channel feature of the inventive variable angle clamp. With this embodiment, the clamp 85 can be mounted on the shank 45 of a bone fastener with the open channel 88 facing along the length of the spinal rod R. A pre-loaded connector 10 can be slid along the length of the bar until the stem of the connector is lodged within the yoke channel 88.

In the illustrated embodiment, the bone fastener is a Schantz screw 45. Of course, it is understood that other types of spinal fasteners are contemplated for use with the clamps 50, 70, 75 or 85 of the present invention. For instance, a spinal hook can be provided with a clamping shank, such as the shank 47 illustrated in FIG. 6. Other elements of a spinal fixation scaffolding can also be adapted for engagement by the variable angle clamp 50. In addition, while the top-tightening connector 10 has been illustrated for use with the clamps of the present invention, other rod-engagement connectors can be utilized. For instance, the clamps of the present invention can be adapted for use with a prior TSRH® system eyebolt and nut arrangement.

It should be understood that the clamps 50, 70, 75 and 85 are all formed of a medical grade and strength material sufficient for implantation as part of a spinal fixation system. It should also be appreciated that the clamps should be formed of the same or compatible material as the variable angle connector. Suitable material can include a fiber reinforced composite, or a metal such as titanium or stainless steel.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For instance, while the clamps of the present invention are integral—i.e., the clamp halves are connected—the clamp halves can be provided as separate components. Thus, the clamp 50 shown in FIG. 7 can be split along the midline M so that halves 52 and 54 are separate pieces. The two pieces can be readily combined to form the clamping portion 64 and particularly the bore 66. The resulting two-piece clamp can be assembled and fixed to the variable angle top-tightening assembly 10 in the same manner as described above.

What is claimed is:

1. An assembly for connecting a bone-engaging fastener to an elongated spinal implant configured to span a length of the spine, the bone engaging fastener having an elongated shank, comprising:
   a connector having a body configured for engagement to the elongated spinal implant and a stem projecting from said body;
   a first surface associated with said connector;
   a second surface associated with said stem; and
   a clamp having a clamping portion defining a bore for receiving the elongated shank therethrough and including a pair of clamp halves forming a slot therebetween that intersects said bore, said clamp halves movable toward each other to substantially close said slot, each of said pair of clamp halves defining an open channel configured for receiving said stem therein with said clamp halves disposed between said first and second surfaces.

2. The assembly according to claim 1, wherein said first surface and an outer surface of one of said clamp halves define a variable angle interengagement feature therebetween.

3. The assembly according to claim 2, wherein said interengagement feature includes interdigitating splines defined on said first surface and said outer surface.

4. The assembly according to claim 3, wherein said connector includes a washer mounted on said body, said washer defining said first surface.

5. The assembly according to claim 1, wherein said stem includes a T-bar, said T-bar defining said second surface.

6. The assembly according to claim 1, wherein said clamping bore includes a surface feature for enhancing the engagement between said bore and the elongated shank.

7. The assembly according to claim 1, wherein said clamping bore is symmetrically disposed relative to said slot.

8. The assembly according to claim 7, wherein said clamp halves are substantially symmetric.

9. The assembly according to claim 7, wherein said clamp halves are asymmetric.

10. The assembly according to claim 1, wherein each of said clamp halves has an outer surface and said clamping bore is substantially symmetrically disposed between said outer surfaces.

11. The assembly according to claim 1, wherein each of said clamp halves has an outer surface and said clamping bore is asymmetrically disposed between said outer surfaces.

12. The assembly according to claim 1, wherein said open channel is substantially parallel with said bore defined in said clamping portion.

13. The assembly according to claim 1, wherein said open channel is substantially perpendicular to said bore defined in said clamping portion.

14. A spinal fixation assembly comprising:
   an elongated rod sized to span a length of the spine;
   at least one bone engaging fastener having an elongated shank; and
   a connector assembly associated with each said at least one bone-engaging fastener including;
      a connector having a body defining a bore for receiving said elongated rod therethrough and a stem projecting from said body;
      a first surface associated with said connector;
      a second surface associated with said stem; and
      a clamp having a clamping portion defining a bore for receiving the elongated shank therethrough and including a pair of clamp halves forming a slot therebetween that intersects said bore, said clamp halves movable toward each other to substantially close said slot, each of said pair of clamp halves defining an open channel configured for receiving said stem therein with said clamp halves disposed between said first and second surfaces.

15. The spinal fixation assembly according to claim 14, wherein said first surface and an outer surface of one of said clamp halves define a variable angle interengagement feature therebetween.

16. The spinal fixation assembly according to claim 15, wherein said interengagement feature includes interdigitating splines defined on said first surface and said outer surface.

17. The spinal fixation assembly according to claim 16, wherein said connector includes a washer mounted on said body, said washer defining said first surface.

18. The spinal fixation assembly according to claim 14, wherein said open channel is substantially parallel with said bore defined in said clamping portion.

19. The spinal fixation assembly according to claim 14, wherein said open channel is substantially perpendicular to said bore defined in said clamping portion.

20. A clamp for use with a spinal implant assembly, the assembly having a spinal rod configured to span a length of the spine, a bone-engaging fastener having an elongated shank, and a variable angle connector having a body defining an opening configured to receive the spinal rod therethrough, a washer mounted on the body having a first surface having a variable angle feature, and a stem projecting from the body, the stem terminating in a T-bar having a second surface facing the first surface, said clamp comprising:
   a clamping portion defining a bore therethrough configured to receive the elongated shank of the bone-engaging fastener therein;
   a pair of clamp halves forming a slot therebetween that intersects said bore, said clamp halves movable toward each other to substantially close said slot and reduce said bore around the elongated shank;
   an outer surface of one of said clamp halves defining a variable angle feature configured for interengagement with the first surface of the washer, and the outer surface of the other of said clamp halves configured for pressure contact with the second surface of the T-bar; and
   an open channel defined in said clamp halves, said open channel configured to receive the stem of the variable angle connector therein when the shank of the bone-engaging fastener extends through said bore.

* * * * *